(12) United States Patent
Bennett

(10) Patent No.: US 9,028,643 B2
(45) Date of Patent: May 12, 2015

(54) METHODS OF BONDING AND ARTICLES FORMED THEREBY

(75) Inventor: Scott Mathew Bennett, Gorham, ME (US)

(73) Assignee: Corning Incorporated, Corning, NY (US)

( * ) Notice: Subject to any disclaimer, the term of this patent is extended or adjusted under 35 U.S.C. 154(b) by 389 days.

(21) Appl. No.: 13/195,266

(22) Filed: Aug. 1, 2011

(65) Prior Publication Data

US 2012/0052311 A1 Mar. 1, 2012

Related U.S. Application Data

(60) Provisional application No. 61/378,168, filed on Aug. 30, 2010.

(51) Int. Cl.
| | |
|---|---|
| *B32B 37/04* | (2006.01) |
| *B32B 13/04* | (2006.01) |
| *B29C 65/00* | (2006.01) |
| *B29C 65/18* | (2006.01) |
| *B29C 65/82* | (2006.01) |
| *G01M 3/32* | (2006.01) |
| *B29C 65/32* | (2006.01) |
| *B29C 65/78* | (2006.01) |

(52) U.S. Cl.
CPC ............. *B29C 66/8322* (2013.01); *B29C 65/18* (2013.01); *B29C 65/32* (2013.01); *B29C 65/8246* (2013.01); *B29C 66/0042* (2013.01); *B29C 66/112* (2013.01); *B29C 66/53461* (2013.01); *B29C 66/71* (2013.01); *B29C 66/7352* (2013.01); *B29C 66/8122* (2013.01); *B29C 66/81261* (2013.01); *B29C 66/8242* (2013.01); *B29C 66/8246* (2013.01); *B29C 66/83221* (2013.01); *B29C 66/91941* (2013.01); *B29C 66/91943* (2013.01); *B29C 66/929* (2013.01); *B29C 66/949* (2013.01); *G01M 3/3272* (2013.01); *B29C 65/7841* (2013.01); *B29C 66/73366* (2013.01); *B29C 66/91651* (2013.01); *B29C 66/91421* (2013.01); *B29C 66/92211* (2013.01); *B29C 66/9241* (2013.01)

(58) Field of Classification Search
CPC ................................ B32B 37/04; B32B 37/06
USPC ......................................... 428/446; 156/308.2
See application file for complete search history.

(56) References Cited

U.S. PATENT DOCUMENTS

| | | | |
|---|---|---|---|
| 3,052,590 A | 9/1962 | Maros et al. | |
| 3,864,892 A * | 2/1975 | Molvar | ........................... 53/478 |
| 4,019,947 A | 4/1977 | Stock et al. | ................... 156/510 |

(Continued)

FOREIGN PATENT DOCUMENTS

| | | | |
|---|---|---|---|
| EP | 1 974 818 A1 | | 1/2008 |
| GB | 2360038 A | * | 9/2001 |
| WO | 2007-093636 A | | 8/2007 |

*Primary Examiner* — Daniel Lee
(74) *Attorney, Agent, or Firm* — Michael Russell

(57) ABSTRACT

A method of bonding a polymer film to a mating part, including:
   placing a mating part in a nest;
   contacting the polymer film and the mating part;
   heating a die including a thermally conductive silicone to a temperature at or above a glass transition temperature of the polymer film, the mating part, or both;
   actuating the die onto the polymer film, wherein the thermally conductive silicone contacts the polymer film and bonds the polymer film to the mating part to form a bonded article; and
   actuating the die away from the polymer film.

18 Claims, 5 Drawing Sheets

(56) References Cited

U.S. PATENT DOCUMENTS

| | | | |
|---|---|---|---|
| 6,719,867 B1 | 4/2004 | Mileti et al. | 156/251 |
| 6,955,739 B2 | 10/2005 | Yamaguchi et al. | 156/273.3 |
| 2008/0118692 A1* | 5/2008 | McLeod et al. | 428/36.92 |

* cited by examiner

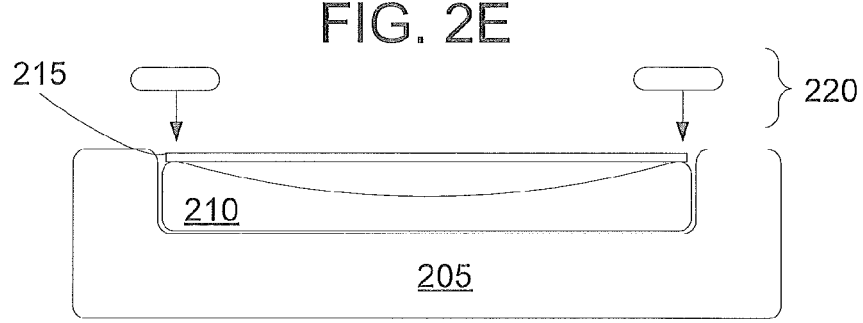
FIG. 2E
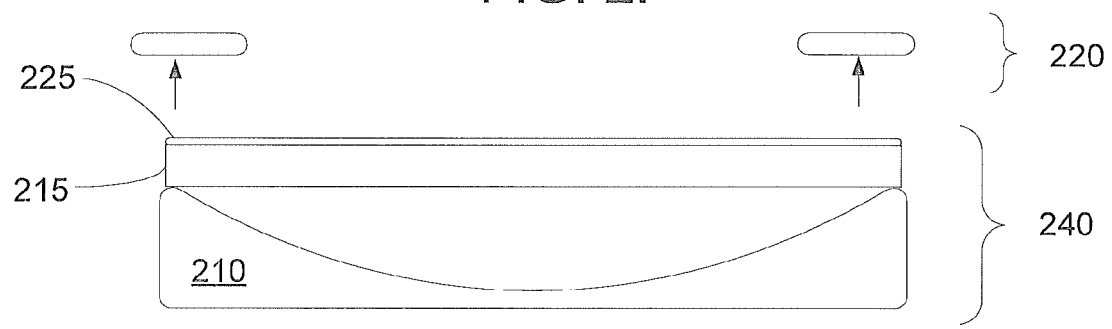
FIG. 2F
FIG. 3
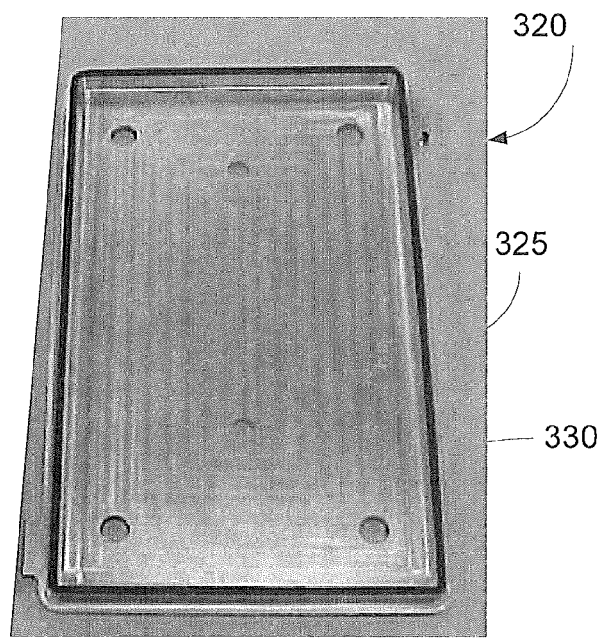

METHODS OF BONDING AND ARTICLES FORMED THEREBY

CROSS-REFERENCE TO RELATED APPLICATION(S)

This application claims the benefit of priority under 35 U.S.C. §119 of U.S. Provisional Application Ser. No. 61/378,168, filed on Aug. 30, 2010, the content of which is relied upon and incorporated herein by reference in its entirety.

BACKGROUND

The disclosure relates to methods of bonding polymer films to parts, and articles formed by the bonding. New methods of bonding plastics together that offer advantages over previously utilized methods are disclosed.

SUMMARY

The disclosure provides a method of bonding a polymer film to a mating part, including: placing a mating part in a nest; contacting a polymer film and the mating part; heating a die to a temperature at or above a glass transition temperature of the polymer film, the mating part, or both, the die comprising a thermally conductive silicone; actuating the die onto the polymer film so that the thermally conductive silicone contacts the polymer film to form a bond between the polymer film and the mating part; and actuating the die away from the polymer film, to form a bonded article.

Also disclosed are articles that include a mating part that includes a first material; a polymer film that includes a second material, and having a first surface and an opposing second surface; a bond that attaches the first surface of the polymer film to the mating part; and a bond region that includes the bond and residual silicone on the second surface of the polymer film.

BRIEF DESCRIPTION OF THE DRAWINGS

In embodiments of the disclosure:
FIGS. 2A through 2F schematically illustrate the article at various steps along an exemplary method;
FIG. 3 depicts an exemplary die.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Embodiments other than those specifically discussed herein are contemplated and may be made without departing from the scope or spirit of the present disclosure. The following detailed description is not limiting. The definitions provided are to facilitate understanding of certain terms frequently used and do not limit the disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g., 1 to 5 includes 1, 1.5, 2, 2.75, 3, 3.80, 4, and 5) and any range within that range.

As used in this application, the singular forms "a", "an", and "the" encompass embodiments having plural referents, unless the content clearly dictates otherwise. The use of a singular form of a term, can encompass embodiments including more than one of such term, unless the content clearly dictates otherwise. For example, the phrase "adding a solvent" encompasses adding one solvent, or more than one solvent, unless the content clearly dictates otherwise. As used in this application, the term "or" is generally employed in its sense including "either or both" unless the context clearly dictates otherwise.

"Include," "including," or like terms means encompassing but not limited to, that is, inclusive and not exclusive.

The disclosure provides methods of bonding polymer films to an article. The article that the polymer film is bonded to is sometimes referred to as a mating part in that the polymer film bonds with the mating part to form a bonded article.

Figure 1:
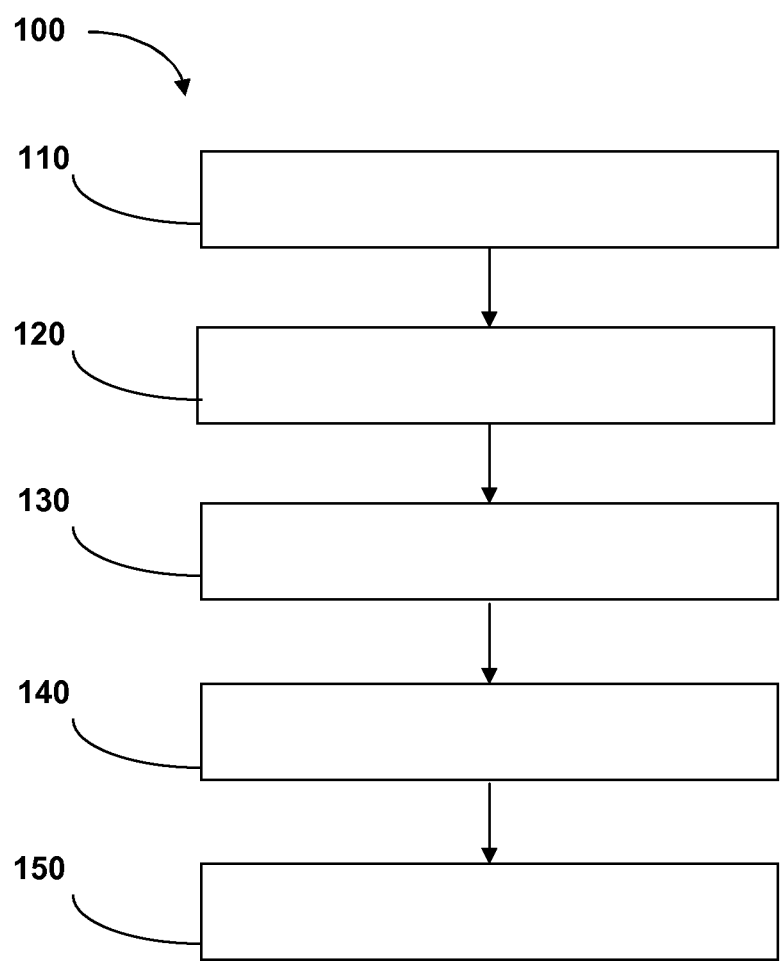
FIG. 1 schematically illustrates a disclosed method.

An exemplary method is depicted in the flowchart 100 in FIG. 1. An exemplary method can include step 110, placing a mating part in a nest, step 120, contacting a polymer film with the mating part, step 130, heating a die, step 140, actuating the die onto the polymer film, and step 150, actuating the die away from the polymer film. Methods as disclosed herein can also include additional steps, including steps disclosed herein and steps not disclosed herein. The steps can be accomplished in any order (that would not be contrary to the step itself), and can be undertaken once or more than once. The steps in the disclosed methods can be carried out, for example, to form a bonded article, as discussed below.

A first step in an exemplary method is step 110, placing a mating part in a nest. The phrase "mating part", as used herein can generally refer to any article that is to be bonded to a polymer film using disclosed methods. A mating part can be, but need not be, part of a larger article. The mating part can be part of, for example, a cell culture apparatus or a multiwell plate of a cell culture apparatus. The mating part can also be any other kind of article or portion of an article or device. Mating parts can generally have any form or shape, which can be dictated only on the ultimate use of the mating part or the bonded article. In embodiments, a mating part can have a three dimensional shape. In embodiments, a mating part is different from a thin film.

In embodiments, a mating part can have an average thickness that is generally greater than 0.0010 inch (25 micrometers (μm)); greater than 0.01 inch (250 μm); greater than 0.1 inch (2.5 millimeters (mm)); or greater than 1 inch (2.5 centimeters (cm)).

Mating parts can be made of numerous types of materials. Generally, mating parts can be plastics or polymeric. Exemplary materials that mating parts can include, for example, polymers or copolymers, for example vinyl polymers such as polyolefins and non-vinyl polymers such as polyesters can be used. More specifically, mating parts can be made of polystyrene, polyethylene, polypropylene, polycarbonate, copolymers thereof, and like polymers, or mixtures thereof. In embodiments, mating parts can be made of polystyrene; and in embodiments, mating parts can be made of a copolymer based on cyclic olefins and ethylene that is commercially available as TOPAS® COC resins (TOPAS Advanced Polymers, Inc., Florence, Ky.). The mating part will have a glass transition temperature (Tg), that will depend on the identity of the polymer (or copolymer).

The first step 110 includes placing a mating part in a nest. The phrase "nest", as used herein can generally refer to any article that can hold a mating part. A nest can support, house, cradle, or otherwise hold a mating part. In embodiments, a nest can provide support for a mating part so that pressure can be exerted on the mating part without detrimentally affecting the mating part. This function of a nest can be analogous to the function an anvil serves. The nest can provide support to the mating part only in the areas where pressure is to be exerted (by the die) or can provide support to the mating part in more than the areas where pressure is to be exerted by the die. In embodiments, a nest can have a surface that at least substantially mirrors at least part of a surface of a mating part.

Nests can generally be made of materials that provide mechanical stability and can withstand at least some pressure being exerted thereon. In embodiments, nests can be made of materials that are generally hard. Exemplary materials can include hard plastics, metals, ceramics, or combinations thereof. In embodiments, nests can be made of aluminum or stainless steel.

Figure 2A:
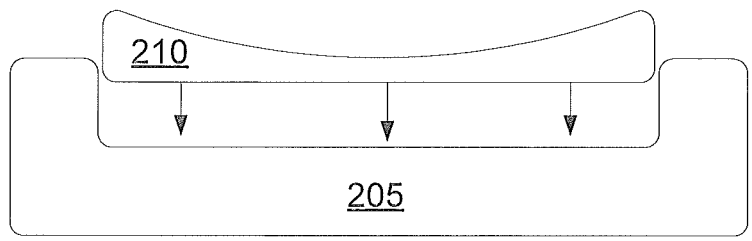

FIG. 2A depicts a cross section of an exemplary mating part and nest. FIG. 2A shows a mating part 210 and a nest 205. The figure depicts the mating part 210 being placed in, or lowered into the nest 205. As seen in this exemplary embodiment, the mating part 210 is housed within the nest 205. It should be noted that the mating part 210 can be placed in the nest 205 either by hand (i.e., a human operator), automatically (i.e., an assembly line type process), or by some combination thereof.

FIG. 1 depicts a second step 120, contacting a polymer film with the mating part. The phrase "polymer film" generally refers to a film of polymer material that has an average thickness of not greater than 0.001 inch (25 microns (μm)). A polymer film can have substantially the same thickness across the entirety of the polymer film or can have different thicknesses across the entirety of the polymer film. A polymer film can include a single layer of a single polymer material or can include more than one layer of one or more than one kind of polymer material. In embodiments, a polymer film can be a polymer film that has a thickness that is not greater than 0.0005 inch (13 microns); or not greater than 0.0001 inch (2.5 microns).

Polymer films can be made of numerous types of materials. Exemplary materials that polymer films can be made of can include both polymers and copolymers, for example vinyl polymers such as polyolefins (both cyclic and linear) and non-vinyl polymers such as polyesters can be used. More specifically, polymer films can be made of polystyrene, polyethylene, polypropylene, polycarbonate, or copolymers thereof. In embodiments, polymer films can be made of polystyrene; and in embodiments, polymer films can be made of a copolymer based on cyclic olefins and ethylene that is commercially available as TOPAS® COC resins (TOPAS Advanced Polymers, Inc., Florence, Ky.). The polymer film can have a glass transition temperature (Tg), that can depend on the identity of the polymer (or copolymer).

In general, mating parts and polymer films that are to be bonded together using the disclosed methods can be made of materials that are compatible. Generally, materials that are compatible can form a bond that has an acceptable strength for the particular application. Compatible polymers can be further described as polymers that would not phase separate if they were blended together. In embodiments, mating parts and polymer films can both be formed of polymers of the same class. For example, both the mating part and the polymer film can be vinyl polymers. In embodiments, both the mating part and the polymer film can be polyolefins; or both the mating part and the polymer film can be polyesters. In embodiments, both the mating part and the polymer film can be the same kind of polymer; for example the mating part and the polymer film can both be polystyrene, polyethylene, polypropylene, polycarbonate, or a copolymer thereof; or the mating part and polymer film can both be the same type of TOPAS® COC resin.

Figure 2B:
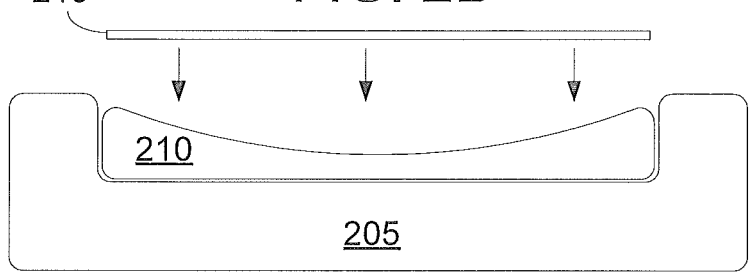
Figure 2C:
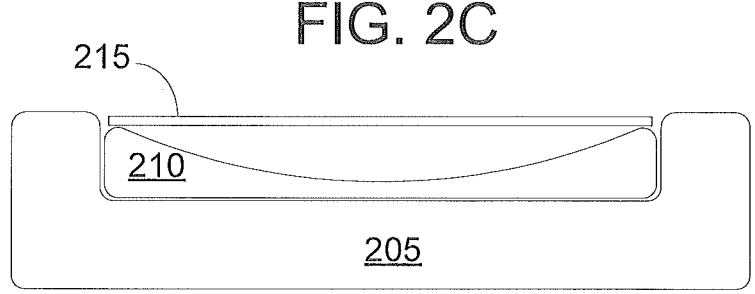

FIG. 2B depicts a cross section of an exemplary mating part 210 and nest 205 with a polymer film 215 being placed into contact with the mating part 210. The particular location where the polymer film 215 contacts the mating part 210 can depend at least in part on the area to be bonded, the type of polymer film and mating part (shapes, materials, thicknesses, etc.), particular aspects of the die, or some combination thereof. It should be noted that the polymer film 215 can be contacted with the mating part 210 either by hand (i.e., a human operator), automatically (i.e., an assembly line type process), or by some combination thereof. FIG. 2C depicts this exemplary article after the polymer film 215 has been contacted with the mating part 210.

FIG. 1 depicts a third step 130, heating a die. A die can include a thermally conductive silicone. Thermally conductive silicone is a silicone containing material that can conduct heat energy. Thermally conductive silicone is commercially available and can have somewhat variable properties. For example, different thermally conductive silicones can have different hardnesses, for example, different durometer measures (e.g., ASTM D2240 type A scales), different tensile strengths, different percents of elongation, different percents of compression sets, different heat resistances, different specific gravities, and different thermal conductivities. The particular type of thermally conductive silicone chosen can depend at least in part on the types of materials (the mating part, the polymer film, or both), the forms (thicknesses, three dimensional shape, etc.) of the mating part and the polymer film, the desired energy and time considerations of the method, or a combination thereof. Exemplary thermally conductive silicones include those commercially available from United Silicone (Lancaster, N.Y.). Specific thermally conductive silicones from United Silicone include, for example, SUPERSIL™ (Red) silicone, ULTRASIL™ (Red) silicone, and THERMOSIL™ (Brown) silicone.

The shape or form of the thermally conductive silicone can depend at least in part on the properties of the thermally conductive silicone, the types of materials (the mating part, the polymer film, or both), the forms (thicknesses, three dimensional shape, etc.) of the mating part and the polymer film, the desired energy and time considerations of the method, or combinations thereof. Generally, the die includes thermally conductive silicone that has a form that is analogous to the bond to be formed, because wherever the thermally conductive silicone contacts the polymer film, the polymer film will be bonded to the mating part. As an example, if a polymer film was to be bonded to all four sides of a rectangular shaped mating part, the thermally conductive silicone can generally have the shape of the outside of the rectangular shaped mating part. The thermally conductive silicone (as well as the die) can generally take any shape, depending at least in part on the shape and form of the polymer film and the mating part.

A die used herein can optionally include other or additional components, including for example additional thermally conductive materials. The optional additional thermally conductive materials can generally transmit heat to the thermally conductive silicone and can function to more easily allow pressure to be applied to the die (and thereby to the polymer film to be bonded), to more easily heat the thermally conductive silicone, or combinations thereof. Exemplary types of additional thermally conductive materials include thermally conductive metals and thermally conductive ceramics. Thermally conductive metals can more specifically include, for example, aluminum and steel. Dies can also optionally include other portions that can, for example, apply force, apply heat, or can allow easy interface with other articles to apply heat or force.

FIG. 3 shows a specific example of an embodiment of a die. The die 320 in FIG. 3 includes thermally conductive silicone 325 that is located on a backer 330. The thermally conductive silicone 325 in this example is formed to create a rectangular shaped bond and is formed of SUPERSIL™ (Red) thermally conductive silicone. The backer 330 in this exemplary die is formed of aluminum and can thereby conduct heat to the thermally conductive silicone 325 and afford a surface to which pressure can be applied to transfer pressure to the polymer film through the thermally conductive silicone 325.

Generally, the die, or more specifically, the thermally conductive silicone portion of the die, can be heated to a temperature that is above the glass transition temperature of the polymer film, the mating part, or both. Generally, thermally conductive silicones can be heated up to 600° F. before the thermally conductive silicone materials are damaged. In embodiments, the die can be heated to a temperature that is at least 50 degrees above the glass transition temperature of the polymer film, the mating part, or both; or at least 100 degrees above the glass transition temperature of the polymer film, the mating part, or both. In embodiments, the die can be heated to a temperature that is above the glass transition temperature of both the polymer film and the mating part; a temperature that is at least 50 degrees above the glass transition temperature of both the polymer film and the mating part; or a temperature that is at least 100 degrees above the glass transition temperature of both the polymer film and the mating part.

The die can generally be heated using known methods, including for example, conduction through a backer (when the die includes an optional backer), or conduction using a heat transfer plate. Conduction through a heat transfer plate contacts the thermally conductive silicone with a heat transfer plate that is not part of the die. Heat can be generated using various, known methods, including for example a resistance heater or an induction heater.

Figure 2D:
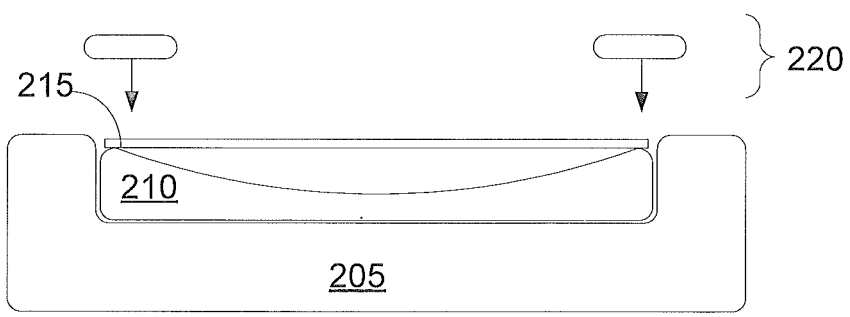

FIG. 2D depicts a cross section of a mating part 210 in contact with a polymer film 215 within a nest 205 with a die 220. The next step 140, includes actuating the die onto the polymer film. The step of actuating is illustrated by the arrows in FIG. 2D. The step of actuating can be accomplished by moving the nest (which holds the mating part and polymer film) towards the die, by moving the die towards the polymer film, or by a combination thereof. The step of actuating the die onto the polymer film can be accomplished by hand (i.e., a human operator), automatically (i.e., an assembly line type process), or by some combination thereof. The step of actuating the die onto the polymer film functions to contact the thermally conductive silicone with the polymer film thereby melting the thin film to the mating part and bonding the two together. This step can also be said to form a bonded article.

The step of actuating the die onto the polymer film can function to apply pressure to the polymer film or can be followed up with the application of pressure onto the polymer film. The amount of pressure to be applied (if any) to the polymer film can depend on a number of factors, including for example the shape and form of the thermally conductive silicone, the properties of the thermally conductive silicone, the types of materials (the mating part, the polymer film, or both), the forms (thicknesses, three dimensional shape, etc.) of the mating part and the polymer film, the desired energy and time considerations of the method, or combinations thereof. In embodiments, pressures as low as 80 Newtons (about 16 pounds force) can be applied to the polymer film from the die. The pressure, if applied can be applied using an air actuator, a servo drive actuator, or like pressure application device. The pressure that is to be applied to the polymer film can also be characterized by the specifications of the pressure application device. For example, in embodiments where an air actuator is used, the bore of the air actuator and the pressure exerted on the actuator can be specified. In embodiments that utilize an air actuator, at least 60 psi (4 Atm) can be exerted onto an air actuator having a 4 inch bore diameter; or 80 psi (5.4 Atm) can be exerted onto an air actuator having a 4 inch bore diameter.

Generally, the die can be maintained in contact with the polymer film for at least an amount of time necessary to form a bond having desirable characteristics. In embodiments, the amount of contact time between the die and the polymer film can depend at least in part on a number of factors, including for example the shape and form of the thermally conductive silicone, the properties of the thermally conductive silicone, the types of materials (the mating part, the polymer film, or both), the forms (thicknesses, three dimensional shape, etc.) of the mating part and the polymer film, the desired energy and time considerations of the method, or combinations thereof. In embodiments where the mating part and polymer film are made of polyolefin types of materials (either cyclic or linear polyolefins), the die can be contacted with the polymer film for at least 3 seconds and generally less than 60 seconds. In embodiments where the mating part and polymer film are made of polystyrene, the die can be contacted with the polymer film for 3 to 30 seconds; for 3 to 10 seconds; or for 3 to 5 seconds. In embodiments where the mating part is made of polystyrene and the polymer film is 0.003 inch (3 mil) TRYCITE™ gas-permeable, polystyrene film (Dow Chemical Company, Midland, Mich.) that has not been further treated, the die can be contacted with the polymer film for 4 seconds.

FIG. 2E depicts a cross section of a mating part 210 (housed in a nest 205) and a polymer film 215 contacted therewith having a die 220 in contact with the polymer film 215. Once the die 220 has been contacted with the polymer film 215 for the desired amount of time, the next step can be undertaken. The next step 150, includes actuating the die away form the polymer film. The step of actuating the die away from the thin film is illustrated by the arrows in FIG. 2F. The step of actuating the die away from the thin film can be accomplished by moving the nest (which holds the mating part and polymer film) away from the die, by moving the die away from the polymer film, or by a combination thereof. The step of actuating the die away from the polymer film can be accomplished by hand (i.e., a human operator), automatically (i.e., an assembly line type process), or by some combination thereof. The step of actuating the die away from the polymer film functions to remove the die from the finished, bonded article. The entire method can be said to form a bonded article, which is shown as bonded article 240 in FIG. 2F.

In embodiments, the die does not need to be cooled before it is actuated away from the polymer film. In other bonding methods it is often necessary or desirable to cool the die before it is actuated away from the polymer film to limit the formation of plastic strings when the die is removed. When plastic strings are produced, the bonded article either has to be subjected to post bonding processes, which can increase the cost of production, or very often has to be scrapped. Disclosed methods offer advantages in that additional cooling time is not necessary and plastic strings are not formed.

Disclosed methods can also include optional steps involving a stripping mechanism. The phrase "stripping mechanism" generally refers to a device, an article, or a combination thereof that affects the location of the bonded article when the die is actuated away from the polymer film. In embodiments, a stripping mechanism can function to make it more likely than not that the bonded article remains with the nest instead of the bonded article being removed from the nest when the die is actuated away from the polymer film.

Embodiments of methods can include a step of contacting a stripping mechanism with a non-bonding region, i.e., a region of the bonded article other than the polymer film that was contacted with the thermally conductive silicone. The non-bonding region can include part of the polymer film, part of the mating part, or some combination thereof. In embodiments, the stripping mechanism can be contacted with a non-bonding region of the mating part. In embodiments, the stripping mechanism can be contacted with the non-bonding region while the die is in contact with the polymer film. The stripping mechanism can be utilized by hand (i.e., a human operator), automatically (i.e., an assembly line type process), or by some combination thereof.

Disclosed methods can also include an optional step of removing the bonded article from the nest. Such an optional step can be undertaken if a stripping mechanism was used or if no stripping mechanism was used. Once the bonded article is removed from the nest, a second mating part may optionally be placed in the nest. Another optional step that can be included in disclosed methods can include reheating the die once it is actuated away from the polymer film. The step of reheating can be undertaken before, after or without use of a stripping mechanism; before, after or without removing the bonded article from the nest; before, after or without placing an additional mating part in the nest; or some combination thereof.

Figure 4:
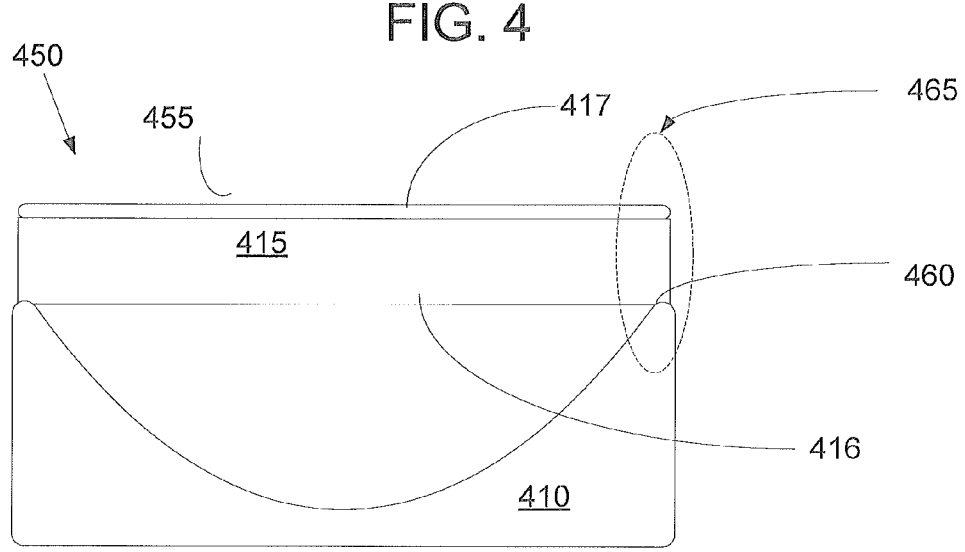
FIG. 4 schematically illustrates an exemplary article.

Also disclosed herein are articles, which can be made using disclosed methods. FIG. 4 shows an article 450 that includes a mating part 410 that is generally made of a first material and a polymer film 415 that is generally made of a second material as generally discussed above. The polymer film 415 includes a first surface 416 and an opposing second surface 417. The article 450 also includes a bond 460. The bond 460 generally functions to attach the first surface of the polymer film to the mating part. The bond 460 is generally formed when the polymer film is contacted with the heated die.

The article 460 also includes a bond region 465. The bond region 465 generally includes the bond 460, a portion of the polymer film 415 and residual silicone that is located on the second surface 417 of the polymer film 415. A residual silicone layer 455 is shown in FIG. 4. It should be noted that the residual silicone layer 455 need not be, but can be located across the entire surface of the polymer film 415 that was in contact with the thermally conductive silicone from the die. In embodiments, the residual silicone can be only intermittently located in the areas of the polymer film 415 where the thermally conductive silicone contacted it. In embodiments, a disclosed article need only have some portion of residual silicone located thereon. In embodiments, the residual silicone was deposited from heated thermally conductive silicone that was contacted with the polymer film.

Disclosed methods and articles can offer numerous advantages. For example, disclosed methods can form relatively strong bonds between the polymer film and mating part; offer decreased process times because of the lack of cooling needed before removing the die; reduce or eliminate the formation of plastic strings and other particulates; reduce damage to the polymer film; provide flexibility in the shapes of mating parts that can be bonded; can compensate for slight surface irregularities in both polymer films and mating parts; or combinations thereof. Similarly, disclosed articles possess advantages because of these and other advantages in the process used to create them.

EXAMPLES

Figure 5:
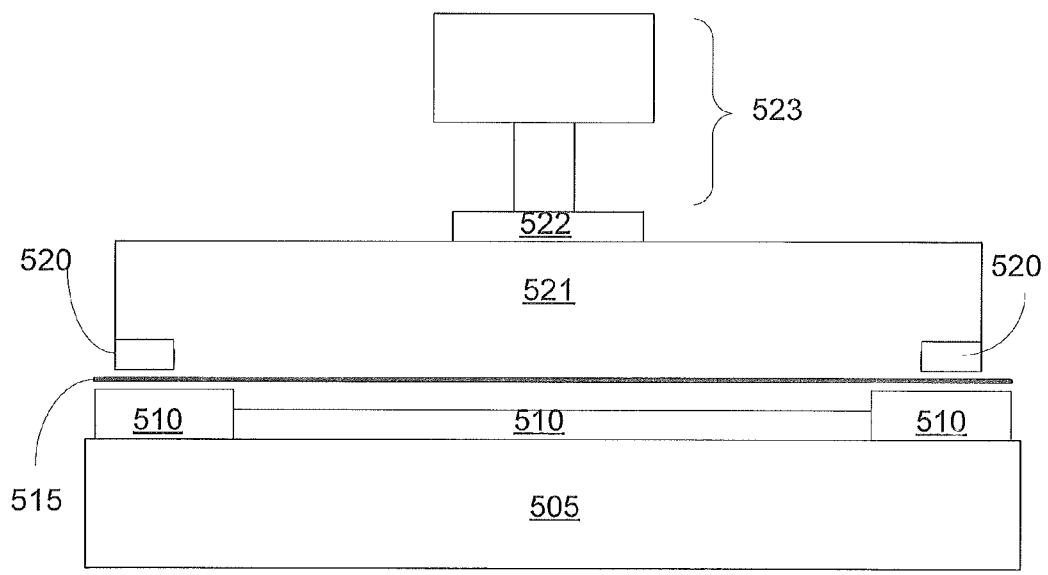
FIG. 5 schematically illustrates a system utilized in the Example.

A system, which is schematically depicted in FIG. 5, was assembled. The system included a nest 505 made of aluminum that was generally shaped to hold a mating part 510 that was made of STYRON® 685D polystyrene (Dow Chemical Company, Midland, Mich.). The mating part 510 was a portion of a HYPERFLASK™ cell culture vessel (Corning Inc., Corning, N.Y.). The system also included a die that had SUPERSIL® thermally conductive silicone 520 and an aluminum backer 521. The backer 521 of the die had a portion of thermally insulating material 522 upon which an actuation device 523 could exert pressure. The polymer film 515 in this example was a 0.003" TRYCITE™ gas-permeable, polystyrene film (Dow Chemical Company, Midland, Mich.) treated to form a CORNING® CellBIND Surface (Corning, Inc., Corning, N.Y.).

Figure 6:
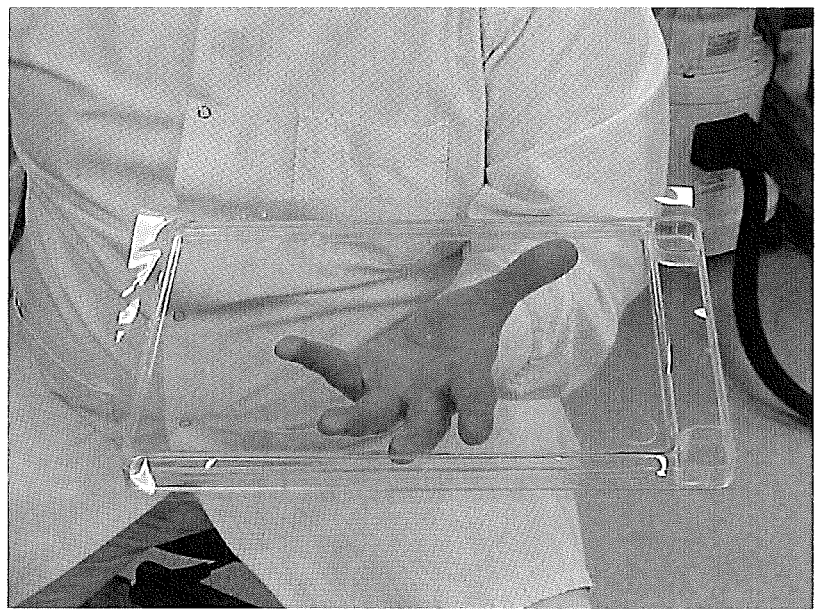
FIG. 6 depicts an exemplary bonded article formed in the Example.

The mating part 510 was first placed in the nest 505 and then the polymer film 515 was placed on the mating part 510. The thermally conductive silicone 520 was then heated, using a resistive heater, to a desired temperature (e.g., 350° C., 375° C., and 400° C.). The heated die was then actuated towards the polymer film until it contacted the polymer film. The die was maintained in contact with the polymer film for a desired time (e.g., 10 sec, 20 sec, and 30 sec), at which point the die was actuated away from the polymer film to form a bonded article. An exemplary bonded article as produced in this Example can be seen in FIG. 6.

Figure 7:
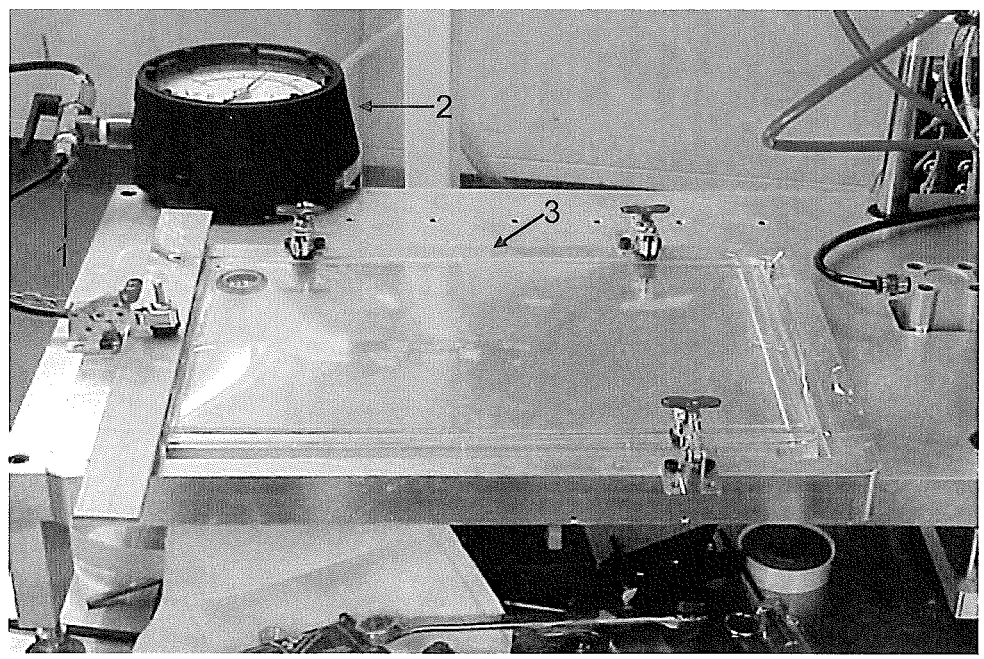
FIG. 7 depicts a leak test fixture utilized in the Example.

The bonded articles were tested for leaks using a leak testing fixture (FIG. 7). Arrow 1 points to the pressure regulator, arrow 2 points to the pressure gauge, and arrow 3 points to the bonded article clamped in the prototype leak test fixture. Bonded articles were tested to 0.5 psi. Table 1 shows the results of the leak testing.

TABLE 1

| Temp.(° C.)/ Time(sec.) | Repetition 1 (PSI loss) | Repetition 2 (PSI loss) | Repetition 3 (PSI loss) | Repetition 4 (PSI loss) | Repetition 5 (PSI loss) |
| --- | --- | --- | --- | --- | --- |
| 350/10 | Leak | Leak | Leak | Leak | Leak |
| 350/20 | 0.00070 | 0.00058 | 0.00038 | 0.00030 | 0.00047 |
| 350/30 | 0.00027 | 0.00061 | Leak | 0.00040 | 0.00046 |
| 375/10 | Leak | Leak | 0.00026 | 0.00025 | 0.00037 |
| 375/20 | Leak | Leak | 0.00042 | 0.00025 | 0.00027 |
| 375/30 | 0.00052 | 0.00027 | 0.00028 | 0.00032 | 0.00030 |
| 400/10 | 0.00021 | 0.00024 | 0.00036 | 0.00026 | 0.00027 |
| 400/20 | 0.00024 | 0.00025 | 0.00029 | 0.00021 | 0.00015 |
| 400/30 | Leak | Leak | 0.00019 | 0.00019 | Leak |

From the results seen here, this mating part and polymer film can be bonded together to form a bond that is acceptable for a particular purpose when the thermally conductive silicone is heated to 375° C. and the die is contacted with the polymer film for 30 seconds.

Additional work was accomplished to bond TRYCITE™ gas-permeable, polystyrene films that were not treated to form a CORNING® CellBIND Surface. Acceptably performing bonds were obtained by heating the die to 375° C. and contacting the die with the polymer film for 4 seconds.

The implementations described above and other implementations are within the scope of the following claims. One skilled in the art will appreciate that the present disclosure can be practiced in embodiments other than those disclosed. The disclosed embodiments are presented for purposes of illustration and not limitation.

What is claimed is:

1. A method of bonding a polymer film to a mating part, comprising:
    placing a mating part in a nest;
    contacting the polymer film and the mating part;
    heating a die consisting essentially of a thermally conductive silicone and a thermally conductive backer to a temperature at least about 100 degrees C. above a glass transition temperature of the polymer film, the mating part, or both, wherein the thermally conductive silicone is located on the backer;
    actuating the die onto the polymer film, wherein the thermally conductive silicone contacts the polymer film and bonds the polymer film to the mating part to form a bonded article; and
    actuating the die away from the polymer film.

2. The method of claim 1, wherein the mating part forms a portion of a cell culture apparatus.

3. The method of claim 1, wherein the polymer film has a thickness that is not greater than about 0.001 inch.

4. The method of claim 1, wherein the polymer film and the mating part comprise the same class of polymer.

5. The method of claim 4, wherein the same class of polymer comprises polystyrene, polyethylene, polypropylene, polycarbonate, mixtures thereof, or copolymers thereof.

6. The method of claim 1, wherein the nest has a surface that conforms to a surface of the mating part.

7. The method of claim 1, wherein the die is heated to at least about 100 degrees C. above the glass transition temperature of the polymer film and the mating part.

8. The method of claim 7, wherein heating the die is accomplished with a resistance heater or an induction heater.

9. The method of claim 1, wherein the backer is aluminum, steel, a thermally conductive ceramic, or combinations thereof.

10. The method of claim 1, wherein once actuated onto the polymer film, the die is maintained on the polymer film for at least about three seconds.

11. The method of claim 1, wherein the die is actuated onto the polymer film with a pressure of at least about 80 Newtons.

12. The method of claim 1, wherein actuating the die away from the polymer film is accomplished without active cooling.

13. The method of claim 1 further comprising contacting a stripping mechanism with a non-bonded region of the mating part while the die is in contact with the polymer film.

14. The method of claim 13, wherein the stripping mechanism maintains the bonded article in the nest when the die is actuated away from the polymer film.

15. The method of claim 1 further comprising removing the bonded article from the nest.

16. The method of claim 15 further comprising placing a second mating part in the nest once the bonded article is removed.

17. The method of claim 1 further comprising reheating the die after it is actuated away from the polymer film.

18. The method of claim 1, wherein the thermally conductive backer comprises a portion of thermally insulating material.

* * * * *